US00PP33888P2

(12) United States Plant Patent
Probst

(10) Patent No.: US PP33,888 P2
(45) Date of Patent: Jan. 18, 2022

(54) ***COREOPSIS* PLANT NAMED 'CANDY STRIPES'**

(50) Latin Name: ***Coreopsis* hybrid**
Varietal Denomination: Candy Stripes

(71) Applicant: Darrell Probst, Hubbardston, MA (US)

(72) Inventor: Darrell Probst, Hubbardston, MA (US)

( * ) Notice: Subject to any disclaimer, the term of this patent is extended or adjusted under 35 U.S.C. 154(b) by 0 days.

(21) Appl. No.: 17/315,078

(22) Filed: May 7, 2021

(51) Int. Cl.
*A01H 5/02* (2018.01)
*A01H 6/14* (2018.01)

(52) U.S. Cl.
USPC ..... Plt./417
CPC ..... *A01H 6/14* (2018.05)

(58) Field of Classification Search
USPC ..... Plt./417
CPC ..... A01H 6/14
See application file for complete search history.

(56) References Cited

PUBLICATIONS

Trademark to "Candy Stripe", for live plants and flowers, U.S. Appl. No. 86/008,258, filed Jul. 11, 2013.*

* cited by examiner

*Primary Examiner* — Anne Marie Grunberg
(74) *Attorney, Agent, or Firm* — Penny J. Aguirre

(57) ABSTRACT

A new cultivar of hybrid *Coreopsis* plant named 'Candy Stripes' that is characherized by its compact plant habit reaching an average of 33 cm in height and 45 cm in width, its floriferous and long blooming season of its nearly sterile inflorescences that do not require deadheading; blooming commences in late-June and lasts until frost in Kensington, Conn., its medium sized inflorescences with ray florets that are pink in color with a cherry red eyezone, its resistance to powdery mildew and leafspot and its cold hardiness at least to U.S.D.A. Zone 4.

2 Drawing Sheets

Botanical classification: *Coreopsis* hybrid.
Variety denomination: 'Candy Stripes'.

BACKGROUND OF THE INVENTION

The present invention relates to a new and distinct cultivar of *Coreopsis* plant, botanically of hybrid origin and known as *Coreopsis* 'Candy Stripes' and will be referred to hereinafter by its cultivar name, 'Candy Stripes'. The new cultivar of *Coreopsis* is an herbaceous perennial grown for landscape and container use.

The new Invention arose from an ongoing controlled breeding program in New Braintree, Mass. The objective of the breeding program is to develop hybrid cultivars of *Coreopsis* with unique and superior garden attributes. In particular, to develop cultivars that are long-lived, sturdy, exhibit a true perennial habit and cold hardy to at least U.S.D.A. Zone 4 in a wide range of flower colors and plant forms.

The Inventor made a controlled cross in August of 2015 in New Braintree, Mass. between an unnamed and unpatented proprietary plant from his breeding program as the female parent (ref. code N2 14-18) and pollen that was pooled from a variety of unnamed and unpatented proprietary plants from his breeding program as the male parent. The exact characteristics of the pollen parent are therefore unknown. 'Candy Stripes' was selected in September of 2016 as a single unique plant amongst the resulting seedlings.

Asexual propagation of the new cultivar was first accomplished by stem cuttings under the direction of the Inventor in Kensington, Conn. in September of 2016. Asexual propagation by stem cuttings has shown that the characteristics of the new cultivar are stable and are reproduced true to type in successive generations.

SUMMARY OF THE INVENTION

The following traits have been repeatedly observed and are determined to be the characteristics of the new cultivar. These attributes in combination distinguish 'Candy Stripes' as a unique cultivar of *Coreopsis*.

1. 'Candy Stripes' exhibits a compact plant habit reaching an average of 33 cm in height and 45 cm in width.
2. 'Candy Stripes' exhibits a floriferous and long blooming season of its nearly sterile inflorescences that do not require deadheading; blooming commences in late-June and lasts until frost in Kensington, Conn.
3. 'Candy Stripes' exhibits medium sized inflorescences with ray florets that are pink in color with a cherry red eyezone.
4. 'Candy Stripes' exhibits resistance to powdery mildew and leafspot.
5. 'Candy Stripes' exhibits cold hardiness at least to U.S.D.A. Zone 4.

The female parent of 'Candy Stripes' differs from 'Candy Stripes' in having flowers that are solid pink in color and in being very fertile causing flower production to stop once seed has set. 'Candy Stripes' can be most closely compared to *Coreopsis* cultivars 'Starlight' (U.S. Plant Pat. No. 28,005) and 'Starstruck' (U.S. Plant Pat. No. 28,006). Both 'Starlight' and 'Starstruck' are similar to 'Candy Stripes' in being resistant to powdery mildew and leaf spot, in having a compact plant habit, and in having a long bloom season that does not require deadheading. 'Starlight' differs from 'Candy Stripes' in having in having inflorescences with creamy white ray florets with a purple eye and in being hardy to U.S.D.A. Zone 5. 'Starstruck' differs from 'Candy Stripes' in having inflorescences that are larger in size with ray florets that are white in color with a large purple eye and in being hardy to U.S.D.A. Zone 5.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Publications include but are not limited to listings on websites by Forest Farm, Egan Gardens, Bill Moore & Company, and Skagit Horticulture.

BRIEF DESCRIPTION OF THE DRAWINGS

The accompanying colored photographs illustrate the overall appearance and distinct characteristics of the new *Coreopsis*. The photographs were taken of 3-month-old plants of 'Candy Stripes' as grown outdoors in a one-gallon container in Belchertown, Mass.

The photograph in FIG. 1 provides a view of plants of 'Candy Stripes' in bloom.

Figure 1:
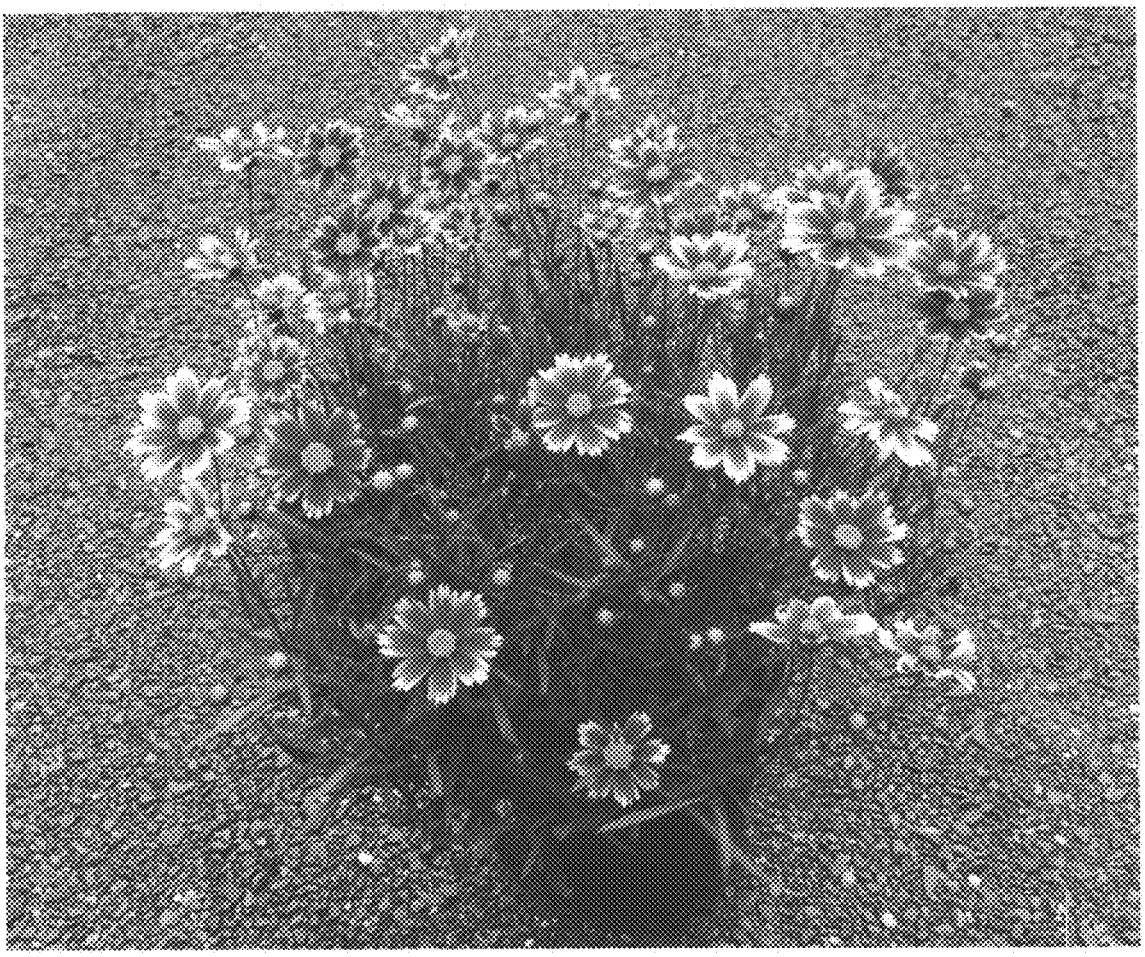
Figure 2:
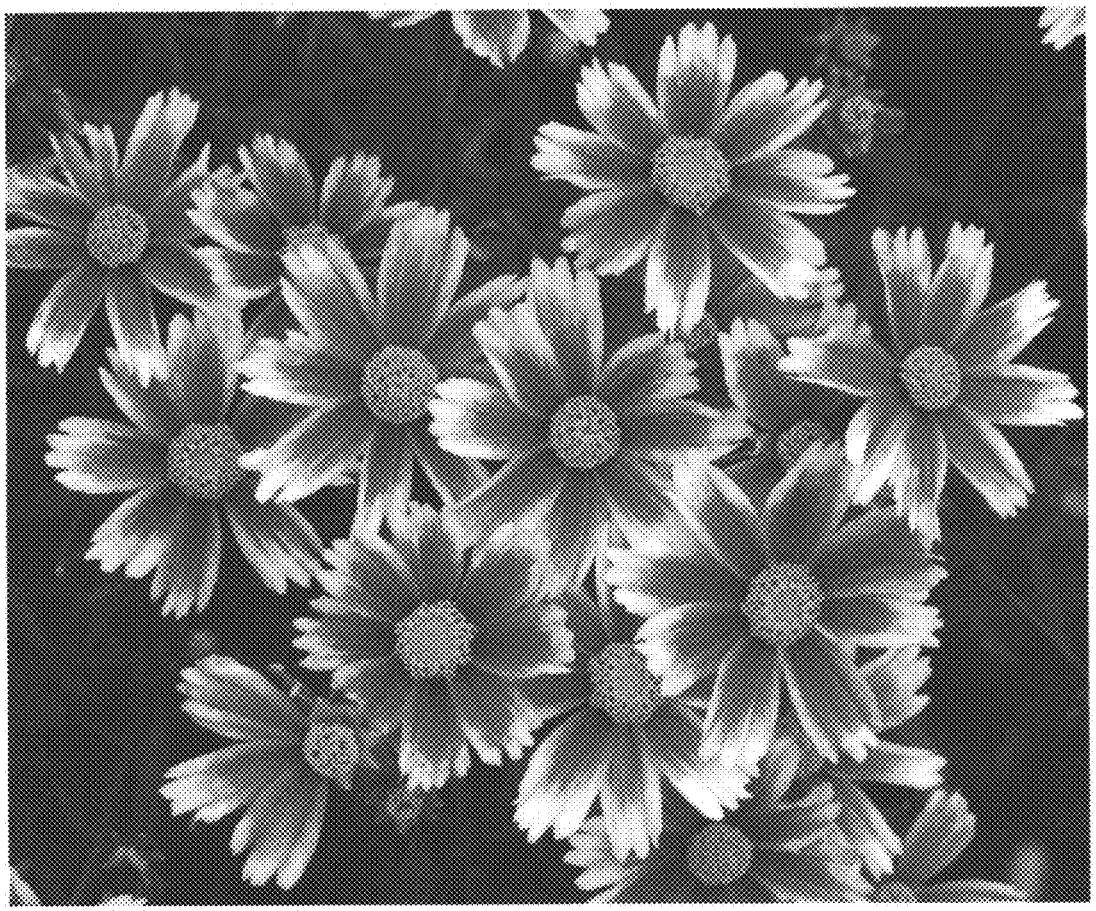

The photograph in FIG. 2 provides a close-up view of the inflorescences of 'Candy Stripes'.

The colors in the photographs are as close as possible with the photographic and printing technology utilized and the color values cited in the detailed botanical description accurately describe the colors of the new *Coreopsis*.

DETAILED BOTANICAL DESCRIPTION

The following is a detailed description of 3-month-old plants of 'Candy Stripes' as grown outdoors in one-gallon containers in Belchertown, Mass. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

- *Blooming period*.—Blooms from late-June until frost in Kensington, Conn.
- *Plant type*.—Herbaceous perennial.
- *Plant habit*.—Clump-forming, compact, upright leafy flowering stems with inflorescences held above the foliage.
- *Height and spread*.—Reaching an average of 32 cm in height and 39 cm in width as grown in a one-gallon container, as a mature plant in the landscape; 33 cm in height, 45 cm in width.
- *Cold hardiness*.—At least to U.S.D.A Zone 4.
- *Diseases and pests*.—Observed to be resistant to powdery mildew (*Podosphaera macularis*) and leafspot (*Pseudomonas cichorii*).
- *Root description*.—Fibrous and fine, NN155A in color.
- *Propagation*.—Stem cuttings.
- *Time required for root initiation*.—An average of 10 days for root initiation.
- *Growth rate*.—Vigorous, but stays compact.

Stem description:

- *Shape*.—Rounded to tetragonal, solid.
- *Stem color*.—144A.
- *Stem strength*.—Strong.
- *Stem size*.—Main stems; an average of 8.5 cm in length and 4 mm in width, lateral stems; an average of 9 cm in length (excluding peduncles) and 4 mm in width.
- *Stem surface*.—Slightly glossy, glabrous.
- *Branching habit*.—Freely branched, an average of 12 basal main stems, lateral stems typically branched as oppositely arranged pairs at each node.
- *Internode length*.—An average of 4 cm.

Foliage description:

- *Leaf division*.—Simple.
- *Leaf margins*.—Entire, bi-fid and trifid.
- *Leaf size*.—Entire leaves; an average of 7 cm in length and 4 cm in width, trifid leaves; center lobe an average of 5 cm in length and 6 mm in width, lateral lobes an average of 2 cm in length and in 2 mm width.
- *Leaf shape*.—Linear.
- *Leaf base*.—Cuneate.
- *Leaf apex*.—Acute.
- *Leaf venation*.—Pinnate, inconspicuous, same color as leaf.
- *Leaf attachment*.—Sessile.
- *Leaf arrangement*.—Opposite.
- *Leaf surface*.—Upper and lower surfaces; dull and sparsely to moderately covered with stiff pubescence, especially along the margins; up to 1 mm in length, NN155A in color.
- *Leaf color*.—Young and mature upper and lower surface; 144A.

Flower description:

- *Inflorescence type*.—Composite with a single row of ray florets surrounding disk florets in the center, forming a radiant head, inflorescences are borne on branch terminals in loose corymbs.
- *Lastingness of inflorescence*.—8 to 10 days until senescence of ray flowers, phyllarys and disk flowers are persistent.
- *Fragrance*.—Moderately pleasant scent.
- *Quantity of inflorescences*.—Free flowering, an average of 4 corymbs per main branch, an average of 3 composites per corymb.
- *Inflorescence size*.—Corymbs; an average of 20 cm in length and 9 cm in width, composite; an average of 2 cm in depth and 4 cm in diameter.
- *Inflorescence buds*.—Globose in shape, an average of 6 mm in depth and diameter, smooth and shiny surface; color; a blend of 148A and NN137A, top 162A.
- *Peduncle*.—Rounded in shape, strong, an average of 11 cm in length and 1.5 mm in diameter, 144A in color, smooth and glabrous surface.

Phyllaries (involucral bracts):

- *Phyllary number*.—1 row of 8.
- *Phyllary arrangement*.—Whorled, 5% of base fused, held horizontal to slightly upwards with the apex and mid-section recurved downwards.
- *Phyllary size*.—An average of 1 cm in length and 4 mm in width.

*Phyllary texture*.—Glabrous and smooth on both surfaces, velvety and transluscent.

*Phyllary color*.—Both surfaces 12A, base 144A.

*Phyllary apex*.—Acute.

*Phyllary base*.—Truncate.

*Phyllary shape*.—Broadly lanceolate.

Ray florets (sterile):

*Number*.—8.

*Shape*.—Oblanceolate, with the appearance of 3 to 4 longitudinal sections.

*Size*.—An average of 2 cm in length and 1 cm in width.

*Apex*.—Rounded with rounded lobes.

*Base*.—Cuneate.

*Margins*.—Entire on sides with lobed and notched apex.

*Aspect*.—Held mainly horizontal and slightly upwards, perpendicular to peduncle.

*Texture*.—Both surfaces; glabrous, dull, and satiny.

*Color*.—Upper surface when opening; base N81A and N77B, mid-section and tips 4A and 4B, upper surface when fully open; base and mid-section 61A, surrounded by 61B and 61C, tips NN155C, lower surface when opening; 5A, lower surface when fully open; 61A and 61B.

Disc florets (male and female):

*Number*.—An average of 60.

*Shape*.—Tubular, corolla is fused, flared and slightly curled at apex.

*Size*.—About 5 mm in length and 0.4 mm in width.

*Color*.—En masse; 24A, individual; corolla (tube) base and mid-section transluscent, 17A and 18D, top below flare 191A, flared portion 13A.

*Receptacle*.—An average of 6.5 mm in diameter and 5 mm in depth, N189B in color.

Reproductive organs:

*Presence*.—Disc florets only.

*Gynoecium*.—1 Pistil; an average of 5 mm in length, style; very fine and 13A in color, bifid pillose, stigma; 13A in color with recurved branches about 0.5 mm in length, ovary is inferior, oblong in shape, an average of 2 mm in length and 1 mm in width, and 145A in color.

*Androecium*.—4 stamens, fused into tube surrounding style, an average of 2 mm in length and less than 0.5 mm in width, 200B in color, pollen; moderate in quantity and 13A in color.

*Seed*.—Seed development has not been observed; presumed to be sterile.

It is claimed:

1. A new and distinct cultivar of *Coreopsis* plant named 'Candy Stripes' as herein illustrated and described.

* * * * *